United States Patent [19]

Doane et al.

[11] Patent Number: 5,120,540
[45] Date of Patent: Jun. 9, 1992

[54] GUSTATORY STIMULANT COMPOSITION AND METHODS OF MAKING AND USING THE SAME

[75] Inventors: Charles C. Doane; Jack W. Jenkins, both of Phoenix, Ariz.

[73] Assignee: Scentry, Inc., Billings, Mont.

[21] Appl. No.: 677,091

[22] Filed: Mar. 29, 1991

[51] Int. Cl.$^5$ .............................................. A01N 65/00
[52] U.S. Cl. ........................... 424/195.1; 424/DIG. 8; 514/558
[58] Field of Search ...................... 424/195.1, DIG. 8; 514/558

[56] References Cited

U.S. PATENT DOCUMENTS

| | | | |
|---|---|---|---|
| 2,957,804 | 10/1960 | Shuyler | 424/7.1 |
| 3,755,600 | 8/1973 | Buchel et al. | 514/521 |
| 3,961,070 | 6/1976 | Davis et al. | 514/521 |
| 4,058,608 | 11/1977 | Zsolnai et al. | 514/521 |
| 4,069,344 | 1/1978 | Karrer | 514/521 |
| 4,320,130 | 3/1982 | Balsley et al. | 514/272 |
| 4,401,266 | 8/1983 | Funkhouser | 239/7 |
| 4,478,848 | 10/1984 | Brandes et al. | 514/521 |
| 4,797,276 | 1/1989 | Herrnstadt et al. | 424/84 |
| 4,880,624 | 11/1989 | Metcalf et al. | 424/84 |

FOREIGN PATENT DOCUMENTS 1195922 10/1985 Canada .

*Primary Examiner*—John W. Rollins
*Attorney, Agent, or Firm*—Finnegan, Henderson, Farabow, Garrett & Dunner

[57] ABSTRACT

A gustatory stimulant composition for beetles of the sub-family Galerucinae comprising a dried and powdered Cucurbitaceae plant material, a lubricant, and an adherent, and a method of making the composition are disclosed. Methods for enhancing the effectiveness of an adulticide used against galerucinid beetles, for controlling a beetle population, and for stimulating the feeding of a beetle population with the composition of this invention are also disclosed.

16 Claims, No Drawings

GUSTATORY STIMULANT COMPOSITION AND METHODS OF MAKING AND USING THE SAME

FIELD OF THE INVENTION

This invention relates to a gustatory stimulant composition for beetles of the sub-family Galerucinae and a method of making the composition. The invention also relates to methods for enhancing the effectiveness of an adulticide used against galerucinid beetles, for controlling a beetle population, and for stimulating the feeding of a beetle population with the composition of this invention.

BACKGROUND OF THE INVENTION

The use of insecticides alone, in particular, adulticides, is common in controlling beetle populations. Typically the insecticide is applied to the soil (as a larvacide) or as a spray on plants (as an adulticide), which the beetle populations would tend to destroy.

The widespread distribution of toxic insecticides for control of crop destructive insects has significant disadvantages. Despite the fact that most continuous corn is treated with insecticides for corn rootworm control, the pest is more prevalent than ever before. Also, conventional soil insecticide treatments are subject to biodegradation and the development of corn rootworm resistance thus decreasing their effectiveness and causing inconsistent performance. In particular, many insecticides are also toxic to birds and other wildlife. Also, current soil larvacides are used mainly in the form of granular or liquid formulations banded in or over seed rows, wherein such practices are major factors in soil and groundwater contamination, a major environmental problem facing the world today.

Furthermore, current insecticide (larvacide and adulticide) applications may have serious deleterious effects on beneficial insects such as lady beetles, lacewings and ground beetles. In other words, many adulticide applications normally decimate the populations of beneficial insects which assist in the control of pest species by predation and/or parasitization.

Finally, most current insecticide applications/ treatments require more than two applications per season for season long control, and this is environmentally and economically undesirable.

In view of the above numerous disadvantages and of increasingly greater demands for environmentally safer means to control beetle populations, it is desirable to provide novel compositions and methods for overcoming the abovedescribed disadvantages.

SUMMARY OF THE INVENTION

It is an object of the present invention to provide a composition, method of making and method of use thereof which reduce the amount of insecticide required to effectively control beetle populations.

It is also an object of the present invention to provide such composition and methods which considerably minimize groundwater contamination.

It is a further object of the present invention to provide a composition and method of use thereof which do not have serious deleterious effects on beneficial insects.

To achieve the objects and in accordance with the purpose of the present invention, as embodied and broadly described herein, the present invention is directed to a gustatory stimulant composition for beetles of the sub-family Galerucinae comprising a dried and powdered Cucurbitaceae plant material, a lubricant and an adherent, and to methods of making and using the composition. An adulticide may further be added to the composition.

The present invention is also directed to a method for enhancing the effectiveness of an adulticide used against galerucinid beetles comprising adding an effective amount of an adulticide to the gustatory stimulant composition.

In addition, the present invention is directed to a method for controlling a beetle population of the family Galerucinae comprising applying a mixture of the gustatory stimulant composition and an effective amount of an adulticide useful against galerucinid beetles to corn plants.

Furthermore, the present invention is directed to a method for stimulating the feeding of a beetle population of the sub-family Galerucinae comprising applying the gustatory stimulant composition to corn plants.

Finally, the present invention is directed to a method of making a gustatory stimulant composition comprising the steps of forming a first layer of a dried and powdered Cucurbitaceae plant material, adding to the first layer a second layer comprising a lubricant, adding to the first and second layers a third layer comprising an adherent, and at the time of use, mixing the first, second and third layers.

Additional objects and advantages of the present invention will be set forth in part in the description which follows. It is to be understood that the general description above and the following detailed description are exemplary and explanatory only and do not limit the present invention, as claimed.

DESCRIPTION OF THE PREFERRED EMBODIMENTS

The composition in accordance with the present invention comprises a dried and powdered Cucurbitaceae plant material, a lubricant and an adherent.

The dried and powdered Cucurbitaceae plant material is obtained from plants of the family Cucurbitaceae, particularly those plants in the genus Cucurbita, including but not limited to *Cucurbita foetidissima, Cucurbita ecuadorensis, Cucurbita martinenzii, Cucurbita palmeri, Cucurbita pedatifolia, Cucurbita palmata* and *Cucurbita okeechobeensis*. Preferably, the plant material is obtained from the gourd and root of the Cucurbitaceae plant.

Constituents of the Cucurbitaceae plants cause compulsive feeding responses in beetle species of the sub-family Galerucinae.

Plants of the family Cucurbitaceae grow wild in such places as southwestern United States and are also planted as crops. Once the Cucurbitaceae plant material is obtained, the plant material is dried, in any suitable manner, e.g.—air-dried for several weeks. Generally, the plant material after drying will have a moisture content of approximately 8% or less by weight.

Once the plant material is dried, the plant material is then chopped up and powdered, e.g.—in a knife mill, hammer mill and/or ball mill, to a mesh size range of about +10 to about +325.

The following mesh size range distribution is preferred:
+10—less than 1% —of plant material
−10+20—1.0%—10% of plant material
−20+100—65%—90% of plant material
−100+200—5%—20% of plant material.

"+" and "−" are commonly used in mesh size specifications. For instance, +100 means that a particle will not pass through a 100 mesh sieve, −100+200 means those particles which will pass through a 100 mesh sieve but will be retained by a 200 mesh sieve.

In the composition, the lubricant is preferably an edible oil and any edible oil may be used. Preferably, a vegetable oil is used, for example, peanut oil, coconut oil, soybean oil or corn oil. One commercially available edible oil typically used is WESSON ® Corn Oil.

The lubricant coats the particles of the dried and powdered Cucurbitaceae plant material preventing the adherent (discussed below) from seeping into the particles. In addition, the oil coats the powder and prevents "crusting" during storage. "Crusting" is the agglomeration of particles causing solid lumps which are deleterious to the effectiveness of the composition because such lumps cause problems in effective mixing of the components and adhesion to the plants.

Furthermore, during application, the lubricant coating the particles also serves to lubricate the application equipment to facilitate the application of the composition and also increases the accuracy with which the product (composition) can be applied.

A suitable adherent for the composition of the present invention is a polybutadiene or other suitable polymer (e.g.—a butadiene polymer or copolymer such as, for example, styrene-butadiene). One such commercially available product is sold by Scentry, Inc. under the registered trademark BioTac®. Such products are often referred to by those skilled in the art as "stickers".

Polybutadiene compounds are available in various viscosities, so that the location of use, and conditions such as the temperature at the time of use will determine which grade will be used in the composition. For instance, BioTac 1® of lower viscosity would be used in the Dakotas whereas BioTac 3® of higher viscosity would be used in Texas.

The adherent causes the composition to adhere to the foliage of the corn plants where the adult beetles are known to feed. Also, the adherent overcomes problems which might arise from rain and overhead irrigation by preventing the product from being washed into the soil where insects are known not to feed. Furthermore, the adherent delays the hardening of the composition, and thus aids in keeping the composition soft and palatable to the insects for several weeks. This is important, since it is known that beetles do not readily feed o hardened products.

METHOD OF PREPARATION

A first layer is formed with the Cucurbitaceae plant material which is dried and powdered. Preferably, the plant material is placed in a container, for example, a 5-gallon plastic container, to form a first layer therein. The container is then agitated , if necessary, to accomplish an even distribution of the plant material and to allow it to settle.

Then, a lubricant is added to the first layer to form a second layer. Preferably, the lubricant, e.g.—oil, is poured on top of the first layer to form a second layer, being careful so as to maintain the integrity of the first layer (i.e.—not having the first layer mix unduly with the second layer).

Once accomplished, the adherent is poured on top of the second layer to form a third layer. Again, the adherent should be carefully poured in order to maintain the integrity of the first and second layers beneath it.

The container is then sealed until use. At the use site, the sealed container is opened and the three layers are thoroughly mixed using either hand stirring or preferably mechanically, e.g.—with an electric drill to which a stirrer has been attached.

Once the three layers are properly mixed, the composition of the present invention is formed, wherein the dried and powdered Cucurbitaceae plant particles are coated with the lubricant, and this mixture in turn coated with the adherent.

Once the three layers have been properly mixed to form the composition, an insecticide, preferably an adulticide, can be added to the composition with thorough mixing. Alternatively, the insecticide can be added to the composition prior to mixing of the three layers, with the composition together with insecticide being mixed.

Any insecticide registered for use on corn rootworm adults may be used as a toxicant in conjunction with the composition of the present invention. Examples thereof include Carbaryl XLR and Sevin 4 oil.

Generally, the amount of insecticide to be used with the composition of the present invention is an effective amount (i.e.—lethal amount) which will effectively kill the beetle population.

Envisaged uses fall into the following per acre ranges, for example, about 10–70 grams of an adulticide (considered in this use to be an effective amount) with about 200–1500 grams of the composition of the present invention.

PROPORTIONS OF THE COMPONENTS

The gustatory stimulant composition of the present invention generally has the following percentage range of composition:

Cucurbitaceae plant material: about 5–70% by total weight of the composition, more preferably about 15–45%, Lubricant: about 5–30% by total weight of the composition, more preferably about 8–10%, Adherent: about 30–60% by total weight of the composition, more preferably about 40–45%.

One embodiment of the present invention includes the use of a filler which is included in the composition of the present invention to replace some of the dried and powdered Cucurbitaceae plant material. Replacing some of the Cucurbitaceae plant material with a filler does not reduce the efficacy of the composition for use as a gustatory stimulant composition.

As a filler, various vegetable substances may be used such as, but not limited to, rice hull flour, wood flour, pecan shell flour and walnut shell flour.

If a filler component is to be used in the composition of the present invention, generally the filler can replace up to about 80% of the Cucurbitaceae plant material.

In other words, the gustatory stimulant composition of the present invention using the filler as an additional component generally would have the following percentage range composition:

Cucurbitaceae plant material: about 1–20% by total weight of the composition, more preferably about 3–10%, Lubricant: about 5–30% by total weight of the composition, more preferably about 8–10%, Adherent: about 30–60% by total weight of the composition, more preferably about 40–45%, Filler: about 4–50% by total weight of the composition, more preferably about 12–35%.

It may be found that the amount of the feeding stimulatory constituents in the plant materials varies greatly depending on several factors including, but not limited to, where they were grown, time of harvest and type of species. In one embodiment and in order to ensure consistent biological activity, water or steam is used to extract the desired constituents from the "gourd root powder" of the plant material. Then, the extract is freeze-dried and reconstituted by adding to a filler described above.

This embodiment in effect produces a concentrated plant material which would be present in an amount less than 1% by total weight of the composition of the present invention, and whereas the filler could replace greater than 99% of the plant material.

Thus, in the embodiment using the concentrated form of the desired Cucurbitaceae plant constituents, the gustatory stimulant composition of the present invention would generally have the following percentage range of composition:

Concentrated Cucurbitaceae plant constituents: about 0.05% by total weight of the composition,
Lubricant: about 5–30% by total weight of the composition, more preferably about 8–10%,
Adherent about 30–60% by total weight of the composition, more preferably about 40–45%,
Filler: about 9–64% by total weight of the composition.

Furthermore, another embodiment of the present invention includes the use of a fungicide, and this would be desirable if, under field conditions, molds were observed to grow on the powdered particles, since such mold growth might cause a direct reduction in efficacy or a reduction in field use longevity.

Typical examples of fungicides which may be used in the present invention include Proxel GXL and Dowicide 1.

The fungicide, if used, would be present in the amount of about 0.1% by weight of the total composition.

The particles of the composition, in any one of its embodiments, upon being formed and distributed, become attached to the foliage of the growing corn. The beetles which are on the corn then randomly encounter and feed on the composition which further stimulates the beetles' feeding. Thus, the beetles feed compulsively on the composition. With an insecticide attached to these particles of the composition, the beetles consume the insecticide attached to the composition which leads to effective control of the beetle population.

Therefore, by adding an effective amount of an insecticide (o adulticide) to the gustatory stimulant composition of the present invention, the effectiveness of an adulticide used against galerucinid beetles is greatly enhanced.

Since the adulticide which is used is added and attached only to the particles of the present composition, only those insects which feed on the gustatory stimulant composition of the present invention would consume the insecticide. This is a primary reason why there is no deleterious effects on beneficial insects such as lady beetles, lacewings, ground beetles and other arthropods since they do not feed on the gustatory stimulant composition of the present invention.

Since beetle feeding is stimulated by the composition of the present invention, when an insecticide is attached to the composition, beetles will compulsively consume the composition and the insecticide and thus smaller amounts of insecticide are required to effectively control a beetle population.

The present invention will be further clarified by the following example, which is intended to be purely exemplary of the present invention.

EXAMPLE

Cucurbitaceae plant material was air dried for several weeks and then chopped up and powdered in a knife mill to a mesh size range of $-100+325$ distributed as follows.

$+100$: 78.13%
$-100+200$: 18.50%
$-200+270$: 3.29%
$-270+325$: 0.08%

4.5 kilograms of this Cucurbitaceae plant material was measured and added into a 5-gallon container. The container was then agitated to ensure an even distribution of the dried and powdered plant material to form a first layer in the container. On top of the plant material layer, 1.0 kilogram of WESSON ® corn oil was carefully poured to form a second layer. Then, 5.0 kilograms of BioTac 1 ® was carefully poured on top of the oil layer to form a third layer. The preparation was conducted at ambient temperatures, and when the addition of the BioTac 1 ® was completed, the container was sealed.

At the use site, the container was opened and the three layers of the formulation were thoroughly mixed using an electric drill to which a stirrer had been attached. At this point, the insecticide, Carbaryl XLR (442 ml) was added to the formulation. Again, the formulation with the insecticide added was thoroughly mixed. The gustatory stimulant composition containing the insecticide was then loaded into a Scentry, Inc. specialized equipment for application onto cornfields (see U.S. Pat. No. 4,262,846).

Field tests of the invention were carried out during the summer of 1990 near Brookings, South Dakota. A cornfield (approximately 125 acres) with the rows running east-west was divided into two large plots, the North plot (48 acres) was treated at the rate of 1.2 lbs of the above formulation plus 0.05 lbs of insecticide per acre (Low Rate) while the South plot (77 acres) was treated with 3.6 lbs of the above formulation and 0.15 lbs of the insecticide per acre (High Rate).

The plots were each divided into four sub-plots, each sub-plot having four observation and sampling rows The sampling rows were a minimum of 30 rows from the dividing border of the two plots, and at least 15 rows apart. Untreated check plots were in adjacent cornfields to the east (East Check) and west (West Check) of the treated field. Efficacy was measured by (a) sampling individual plants and determining the numbers of live beetles present, (b) determining the number of corn rootworms caught in yellow sticky traps, and (c) monitoring the numbers of dead beetles accumulated in tray traps. In addition, the population of the beneficials, lady beetles and green lacewings was monitored.

The visual yellow sticky traps were placed in the middle of the observation plots at a height of about 3.5 feet above the soil. The dead beetle traps were $29 \times 38 \times 1$ inches and covered with 28 mesh screening. Sampling of the corn plants was carried out on five plants in each of the four observation rows, giving 20 plants per replication which, since there were four subplots provided a total of 80 plants per data point per treatment. All beetle data refers to combined western and northern corn rootworms.

Determination of live beetles on the corn plants

Mean number of live beetles/plant (80 data points/observation)

| Date of observation | West Check | East Check | Low Rate | High rate |
|---|---|---|---|---|
| August 6 | 1.6 | 3.7 | 3.6 | 4.0 |
| August 7 | 3.9 | 4.2 | 4.3 | 2.5 |
| August 8 | Day of the application | | | |
| August 10 | 4.2 | 6.8 | 0.2 | 0.0 |
| August 11 | 6.4 | 7.0 | 0.3 | 0.1 |
| August 13 | 2.6 | 5.0 | 1.2 | 0.0 |
| August 14 | 5.5 | — | 1.9 | 1.0 |
| August 15 | 5.7 | 5.7 | 1.5 | 0.5 |
| August 17 | 6.0 | 3.0 | 1.3 | 1.0 |
| August 18 | 5.6 | 4.0 | 1.5 | 1.0 |
| August 21 | 5.8 | 7.0 | 1.6 | 1.6 |
| August 23 | 7.0 | 4.8 | 1.8 | 1.5 |
| August 25 | 6.0 | 3.7 | 2.2 | 1.5 |
| August 28 | 4.8 | 3.3 | 1.6 | 2.2 |

The mean number of beetles/plant in all four plots prior to the application was 3.48 (range 2.75-3.95); the mean number of beetles/plant up to 20 days post application:

West Check—5.43 East Check—5.34 Low Rate—1.28 High Rate—0.87

This indicates a significant reduction in beetle population caused by application of the composition of the present invention; the low rate gave a control factor of 76.25% and the high rate gave a control factor of 84.01%. Control Factor=[(Control—Treatment)÷Control]×100

Determination of beetles caught on sticky traps

Mean number of beetles caught on sticky strap (4 traps per data point)

| Date of observation | West Check | East Check | Low rate | High rate |
|---|---|---|---|---|
| August 6 | 2 | — | 9 | 10 |
| August 7 | 10 | 12 | 14 | 10 |
| August 8 | 34 | 40 | 46 | 35 |
| August 9 | 23 | 22 | 0 | 0 |
| August 10 | 32 | 52 | 0 | 0 |
| August 11 | 40 | 72 | 0 | 0 |
| August 13 | 22 | 90 | 0 | 0 |
| August 14 | 58 | — | 3 | 0 |
| August 15 | 35 | 93 | 4 | 0 |
| August 17 | 54 | 60 | 9 | 7 |
| August 18 | 22 | 56 | 8 | 8 |
| August 21 | 51 | 57 | 10 | 9 |
| August 23 | 70 | 57 | 10 | 9 |
| August 25 | 41 | 29 | 10 | 9 |
| August 28 | 37 | 27 | 14 | 15 |

The mean number of beetles trapped in all plots prior to the application was 20.67 (range 15.33-26.0). The mean number of beetles trapped per observation day up to 20 days post application was:

West Check—40.42 East Check—55.91 Low Rate—5.42 High Rate 4.42

These data indicate a Percentage Control Factor in the upper 80's for the low rate and in the 90's for the high rate.

Determination of dead beetles in tray traps

The mean number of beetle bodies per observation point (4 traps per data point)

| Observation date | West Check | East Check | Low Rate | High rate |
|---|---|---|---|---|
| August 9 | 0 | 1 | 19 | 20 |
| August 10 | 0 | 1 | 24 | 25 |
| August 11 | 2 | 2 | 25 | 27 |
| August 13 | 2 | 2 | 25 | 28 |
| August 14 | 3 | — | 28 | 29 |
| August 15 | 3 | 2 | 29 | 29 |
| August 17 | 3 | 2 | 33 | 33 |
| August 18 | 3 | 2 | 35 | 34 |
| August 21 | 3 | 2 | 34 | 35 |
| August 23 | 3 | 2 | 35 | 37 |
| August 25 | 3 | 2 | 35 | 39 |
| August 28 | 3 | 2 | 35 | 40 |

These dead body counts were undertaken from the day following application of the composition of the invention. The mean numbers of dead beetles was:

West Check—2.33 East Check—1.82 Low Rate—29.75 High Rate—31.3

These data clearly demonstrate the effectiveness of the present invention.

Determination of the effect on beneficial insects

This was monitored by counting the numbers of lady beetles and green lacewings caught on the sticky traps. Each data point represents the mean of 4 observations on that particular date.

| Observation date | West Check | East Check | Low Rate | High rate |
|---|---|---|---|---|
| August 8 | 0.4 | 0.4 | 1.8 | 1.2 |
| August 9 | 0.4 | 0.6 | 2.0 | 1.3 |
| August 10 | 0.6 | 0.6 | 2.1 | 1.5 |
| August 11 | 1.1 | 1.1 | 2.5 | 1.9 |
| August 13 | 1.5 | 2.0 | 3.0 | 2.5 |
| August 14 | 1.5 | — | 3.3 | 2.7 |
| August 15 | 2.0 | 3.0 | 3.7 | 3.3 |
| August 17 | 3.5 | 3.8 | 4.2 | 4.4 |
| August 18 | 3.5 | 4.2 | 5.5 | 5.9 |
| August 21 | 3.5 | 4.2 | 5.5 | 5.9 |
| August 23 | 3.7 | 5.0 | 5.6 | 7.0 |
| August 25 | 3.7 | 5.3 | 5.8 | 7.5 |
| August 28 | 3.9 | 5.5 | 5.9 | 7.8 |

As can be seen from the above table, the mean numbers of beneficial insects in each of the treatments were:

West Check—2.25 East Check—2.96 Low Rate—3.88 High Rate—4.0 and this clearly demonstrates that the application of the composition of the present invention had no deleterious effects on the populations of beneficial insects.

Based on this example, it is readily seen that practice of the present invention reduces the amount of insecticide usage. In addition, the use of the composition of the present invention with an insecticide is efficacious for more than three weeks, thus giving season-long control of the target pest, whereas conventional treatments require more than two applications for season-long control. Thus, insecticide usage when practicing the present invention is only 2.3% of that used for conventional adult sprays.

Furthermore, there is a great reduction in the contamination of soil and groundwater since the composition of the present invention with an insecticide contains less insecticide, (since this insecticide is only associated with the composition of the present invention) and also rain and/or irrigation practices do not wash the composition of the present invention containing the insecticide off the foliage of the corn plants and into the soil.

Finally, there is little or no deleterious effect on beneficial insects such as lady beetles, lacewings, ground beetles and other soil arthropods. Conventional adulticide applications normally decimate the populations of beneficial insects which exist in the control of pest species by predation and/or parasitization. However, by using the composition of the present invention with an adulticide, the insecticide focuses only on the target test species since none of the parasites or predators are influenced by the gustatory stimulant composition of the present invention and the insecticide used in conjunction with the composition of the present invention is only associated with particles of the composition.

Other embodiments of the invention will be apparent to those skilled in the art from a consideration of the specification and practice of the invention discussed herein. It is intended that the specification and example be considered as exemplary only, with the true scope and spirit of the invention being indicated by the following claims.

What is claimed is:

1. A method for enhancing the effectiveness of an adulticide used against galerucinid beetles comprising adding an effective amount of said adulticide to a gustatory stimulant composition comprising a dried and powdered Cucurbitaceae plant material, a lubricant and an adherent.

2. A method for controlling a beetle population of the sub-family Galerucinae comprising applying to corn plants a mixture of an effective amount of an adulticide used against galerucinid beetles and a gustatory stimulant composition comprising a dried and powdered Cucurbitaceae plant material, a lubricant and an adherent.

3. A method for stimulating the feeding of a beetle population of the sub-family Galerucinae comprising applying to corn plants a gustatory stimulant composition comprising a dried and powdered Cucurbitaceae plant material, a lubricant and an adherent.

4. The method according to either of claim 1, 2 or 3 wherein said composition further comprises an insecticide.

5. The method according to claim 4 wherein said composition further comprises a filler.

6. The method according to claim 1 wherein said composition further comprises a fungicide.

7. The method according to either of claims 1, 2 or 3 wherein said composition further comprises a filler.

8. The method according to claim 7 wherein said composition further comprises a fungicide.

9. The method according to either of claim 1, 2 or 3 wherein said composition further comprises a fungicide.

10. The method according to either of claims 1, 2 or 3 wherein said dried and powdered Cucurbitaceae plant material is from the genus Cucurbita.

11. The method according to either of claims 1, 2 or 3 wherein said lubricant is an edible oil.

12. The method according to either of claims 1, 2 or 3 wherein said plant material is a powder of from about +10 to about +325 mesh.

13. The method according to claim 12, wherein said mesh size range for said plant material has the following distribution:

+10—less than 1% —of plant material
−10 +20—1.0% —10% of plant material
−20 +100—65% —90% of plant material
−100 +200—5% —20% of plant material 14. The method according to either of claims 1, 2 or 3, wherein said lubricant is a vegetable oil.

15. The method according to either of claims 1, 2 or 3, wherein said adherent is a polybutadiene compound.

16. The method according to either of claims 1, 2 or 3, wherein said plant material is present in an amount of from about 5–70% by weight; said lubricant is present in an amount of from about 5–30% by weight; and said adherent is present in an amount of from about 30–60% all by weight of said composition.

* * * * *

UNITED STATES PATENT AND TRADEMARK OFFICE
CERTIFICATE OF CORRECTION

PATENT NO. : 5,120,540

DATED : June 9, 1992

INVENTOR(S) : Charles C. DOANE et al.

It is certified that error appears in the above-identified patent and that said Letters Patent is hereby corrected as shown below:

```
    Claim 6, column 10, line 9, change "claim 1" to
-- claim 4 --.
```

Signed and Sealed this

Twentieth Day of September, 1994

Attest:

BRUCE LEHMAN

*Attesting Officer*                *Commissioner of Patents and Trademarks*